(12) United States Patent
Lynch, Jr.

(10) Patent No.: US 9,162,032 B2
(45) Date of Patent: Oct. 20, 2015

(54) SYSTEMS AND METHODS FOR DIAGNOSING AND TREATING SLEEP DISORDERS

(76) Inventor: William Ray Lynch, Jr., Middletown, DE (US)

( * ) Notice: Subject to any disclaimer, the term of this patent is extended or adjusted under 35 U.S.C. 154(b) by 713 days.

(21) Appl. No.: 13/423,957

(22) Filed: Mar. 19, 2012

(65) Prior Publication Data
US 2012/0247472 A1 Oct. 4, 2012

Related U.S. Application Data

(60) Provisional application No. 61/454,878, filed on Mar. 21, 2011.

(51) Int. Cl.
*A61M 11/00* (2006.01)
*A61M 16/00* (2006.01)
*G06F 19/00* (2011.01)

(52) U.S. Cl.
CPC ............. *A61M 16/00* (2013.01); *G06F 19/345* (2013.01); *G06F 19/3406* (2013.01); *G06F 19/3418* (2013.01); *G06F 19/3481* (2013.01); *A61M 2016/0033* (2013.01); *A61M 2205/3553* (2013.01); *A61M 2205/3584* (2013.01); *A61M 2205/3592* (2013.01); *A61M 2205/52* (2013.01); *A61M 2205/84* (2013.01); *A61M 2230/205* (2013.01)

(58) Field of Classification Search
CPC ................... A61M 16/0051; A61M 2230/005; A61M 16/00; A61M 2016/0033; A61M 2205/3553; A61M 2205/3584; A61M 2205/3592; A61M 2205/52; A61M 2205/84; A61M 2205/205; G06F 19/3406; G06F 19/3418; G06F 19/345; G06F 19/3481
USPC ............................ 128/204.18, 204.21, 204.23
See application file for complete search history.

(56) References Cited

U.S. PATENT DOCUMENTS

| 7,118,536 B2 | 10/2006 | Haberland et al. |
| 7,469,697 B2 | 12/2008 | Lee et al. |
| 7,708,697 B2 | 5/2010 | Wilkinson et al. |

(Continued)

FOREIGN PATENT DOCUMENTS

WO   WO 2009114755   9/2009

OTHER PUBLICATIONS

Berry, et al., "The Use of Auto-Titrating Continuous Positive Airway Pressure for Treatment of Adult Obstructive Sleep Apnea," http://www.journalsleep.org/Articles/250204/pdf.

(Continued)

*Primary Examiner* — Steven Douglas
(74) *Attorney, Agent, or Firm* — RatnerPrestia (57) ABSTRACT

A method for diagnosing and treating sleep disorders with a sleep therapy auto-titrator for in-home use by the patient includes the step of collecting, recording and analyzing sleep data in real time with the auto-titrator. Corrective action is provided in real time to the patient to mitigate sleep events based upon the collected sleep data. The collected sleep data is transmitted, via a global computer information system, to a remote server for storage. The stored sleep data is analyzed by a computer programmed with an algorithm to monitor therapy effectiveness daily and for identifying one or more therapy intervention recommendations. An alert is provided to at least one of the patient or a sleep therapy professional associated with the patient communicating the one or more intervention recommendations.

20 Claims, 9 Drawing Sheets

(56) References Cited

U.S. PATENT DOCUMENTS

| | | | |
|---|---|---|---|
| 7,717,112 | B2 | 5/2010 | Sun et al. |
| 7,757,690 | B2 | 7/2010 | Stahmann et al. |
| 7,942,824 | B1 | 5/2011 | Kayyali et al. |
| 7,993,279 | B2 | 8/2011 | Hartley et al. |
| 8,021,309 | B2 | 9/2011 | Zilberg |
| 2004/0244807 | A1 | 12/2004 | Sun et al. |
| 2005/0268912 | A1 | 12/2005 | Norman et al. |
| 2006/0178590 | A1 | 8/2006 | Hebblewhite et al. |
| 2008/0000475 | A1 | 1/2008 | Hill |
| 2008/0015455 | A1 | 1/2008 | Bowman et al. |
| 2008/0041383 | A1 | 2/2008 | Matthews et al. |
| 2008/0059394 | A1 | 3/2008 | El Solh |
| 2008/0146893 | A1 | 6/2008 | Levendowski et al. |
| 2009/0078257 | A1 | 3/2009 | Bhat et al. |
| 2009/0139523 | A1 | 6/2009 | Ayappa et al. |
| 2010/0101583 | A1 | 4/2010 | Chen et al. |
| 2010/0161354 | A1 | 6/2010 | Lim et al. |
| 2011/0192400 | A9* | 8/2011 | Burton et al. ............ 128/204.23 |
| 2011/0297156 | A1 | 12/2011 | Shelly et al. |
| 2013/0333696 | A1* | 12/2013 | Lee et al. ................ 128/200.24 |
| 2014/0116438 | A1* | 5/2014 | Reed ...................... 128/204.21 |

OTHER PUBLICATIONS

Desai et al., "Accuracy of Auto-Titrating CPAP to Estimate the Residual Apnea-Hypopnea Index in Patients with Obstructive Sleep Apnea on Treatment with Auto-Titrating CPAP," http://www.ncbi.nlm.nih.gov.

Fletcher et al., "Unattended home diagnosis and treatment of obstructive sleep apnea without polysomnography," http://www.ncbi.nlm.nih.gov.

Brown, Esq., Daniel B., "Home Testing Demystification," Sleep-Review, Mar. 2010, pp. 1-5.

* cited by examiner

FIGURE 1 (100)

OUTPUT
FIGURE 2 (200)

Usage – (these are Daily Machine Usage in minutes for all Therapy Modes)
    Total Connected Time
    Total Blower Time
    Total Humidifier Time Indices – (these are Daily Indices for all Therapy Modes)
    Apnea/Hypopnea Index
    Apnea Index
    Hypopnea Index
    Obstructed Airway Apnea Index
    Clear Airway Apnea Index
    Non-Responsive Apnea/Hypopnea Index
    Flow Limitation Index
    RERA Index
    Variable Breathing Index Therapy – (these are Daily Therapy Averages for all Modes)
    % Periodic Breathing
    Average leak
    Maximum Leak
    90% Leak
    Average Large Leak Duration
    Total Large Leak Duration
    Total Apnea Duration
    Total Titration
        <u>If ASV</u>
        % Cheyne-Stokes Respiration
        % Triggered Breaths
        Average Peak Flow
        Average Breath Rate
        Average Exhaled Tidal Volume
        Average Inhaled Tidal Volume
        Average Minute Ventilation Device (these are Daily Device Averages actual performance within the set limits)

| If CPAP | If Bi-PAP | If ASV |
|---|---|---|
| Flex Setting | Average IPAP Pressure | Breath Rate |
| Average CPAP Pressure | Minimum IPAP Pressure | Minimum Pressure Support |
| Minimum CPAP Pressure | Maximum IPAP Pressure | Maximum Pressure Support |
| Maximum CPAP Pressure | 90% IPAP Pressure | Maximum Ventilator Pressure |
| 90% CPAP Pressure | Average EPAP Pressure | |
| | Minimum EPAP Pressure | |
| | Maximum EPAP Pressure | |
| | 90% EPAP Pressure | |

SYSTEMS AND METHODS FOR DIAGNOSING AND TREATING SLEEP DISORDERS

CROSS-REFERENCE TO RELATED APPLICATIONS

This application claims priority to Provisional Patent Application Ser. No. 61/454,878 filed Mar. 21, 2011, by William Lynch, Jr., hereby incorporated by reference in its entirety.

FIELD OF THE INVENTION

The present invention relates to systems and methods of diagnosing and treating sleep disorders through the in-home use of an auto-titrator.

BACKGROUND OF THE INVENTION

Obstructive sleep apnea is a significant chronic disease which pervasively effects the general population. The projected rate of sleep apnea in the general population, comparable to the rates of hypertension and obesity, is higher than the rates of breast cancer and diabetes combined. The prevalence of obstructive sleep apnea, however, is obscured due to poor screening and poor public awareness. Among middle-aged individuals, many of the women and men who have moderate to severe sleep apnea have not been screened, identified, or diagnosed.

Individuals with untreated sleep disorders are at higher risks for associated chronic conditions which lead to significant increased health care costs, disability, and even death. Included among these heightened risks are hypertension, stroke, sudden death at night, any cardiovascular death, auto accidents, and work place accidents. These undiagnosed individuals utilize significantly more healthcare costs than their counterparts of the same-age without a sleep disorder. Among adults from 18 to 34 years old, approximately half report that daytime sleepiness interferes with their daily work resulting in significant productivity losses. Employees with excessive daytime sleepiness are also more likely to be involved in an occupational accident. Fatal and non-fatal occupational injuries detract from revenue in the forms lost wages and productivity, administrative expenses, healthcare, and other costs.

Today sparingly few individuals with obstructive sleep apnea are identified and treated. When the few are treated, it is uncommon to collect or utilize information obtained from home sleep therapy machines to determine therapy effectiveness. Even when the electronic data is accessed for a report, the individual's rights of privacy/security of their electronic data are not protected as required by recent Federal regulations, such as the HIPAA HITECH Act. The lack of compliance in this regard results in poor data preservation, often leading to the loss of the electronic data both to the patient and to other future point of care providers.

There are multiple devices, products, and services in the area of sleep disorders, but current technology is inefficient, costly, and ineffective.

The conventional steps to diagnose a consumer with a sleep disorder start with the Primary Care Physician (PCP) or specialist identifying the need for testing to diagnose a sleep disorder. This is affected by physician awareness, i.e., if the physician thinks to asks the screening questions, and if they think treating a sleep disorder is important, then they will pursue a diagnosis. The current identification of consumers with possible sleep disorders has produced the under-diagnosis rate of 93% for females and 82% for males.

Next, the physician may request a sleep study, and the first polysomnogram (PSG) is usually performed in a sleep laboratory. Because of poor access and availability, the time for scheduling is the first delay among a series of weeks to months of delays to diagnose and treat the sleep disorder. The patient arrives to an unfamiliar facility and is wired for data collection. While the consumer is sleeping a technician will assist in collecting the multiple channels of complex information. The technician's training can vary from: on-the-job training with no medical background requirement; no medical background and an 80 hour American Academy of Sleep Medicine (AASM) A-STEP course; healthcare professionals cross-trained for sleep disorders with no course requirements; and meeting the required work period and passing the registry exam to earn the credentials of Registered Polysomnographic Technologist (RPSGT). The unqualified or under qualified technician can produce "Therapy Errors" as described below.

At some facilities, technicians or technologists simply record signals and monitor the patient during the PSG. At other facilities, the technicians/technologists are responsible for staging the sleep changes and scoring any respiratory, cardiac, or limb events which occur during sleep. Due to the differences in the levels of knowledge and performance, the results and accuracy of the studies may vary greatly. This leads to poor inter-scorer reliability of the technicians and unreliable quality of the studies. The medical director is responsible for interpreting the study. Currently there is no inter-rater reliability quality monitoring for physicians providing the interpretations.

The referring physician will request an office visit to review the results—a second delay in diagnosis and treatment. Once diagnosed with sleep-disordered breathing the consumer returns to the sleep lab for a second study to determine the level of Continuous Positive Airway Pressure (CPAP), which results in a third delay in diagnosis and treatment. This second study is called a CPAP titration. If the technicians fail to accurately score—or do not score at all—while titrating pressures, the study often results in Therapy Errors with unnecessarily high CPAP pressures.

The home therapy begins with the consumer obtaining a prescription from a physician for a sleep therapy machine. The referring physician will request an office visit to review the results and write the prescription—a fourth delay in diagnosis and treatment. The most common requested device is a fixed pressure machine, which is dated technology. This equipment is provided to the consumer by a durable medical equipment provider. The equipment can be delivered to the consumer's home by anyone or even mailed. Decisions by the equipment company regarding which machine to place in the consumer's home may lead to consumers receiving low quality sleep therapy machines and even different machines from the one requested in the physician's order. Once delivered, the majority of consumers receive no monitoring or follow-up, especially middle-aged consumers, for whom the healthcare system typically does not reimburse for nor encourage extra monitoring. After a rental period the equipment is owned by the consumer.

HITECH sleep therapy machines capture sleep therapy data in onboard memory systems. The machine can collect sleep therapy data on a digital memory storage device similar to those used for a digital camera. Unless the physician or the equipment company has a card reader to download the information to be reviewed, the data remains in the sleep therapy machine. If the information is downloaded for a report, the card is erased and the past data is lost to any future point of care provider. Thus, data collection remains quite limited.

Another alternative is to collect the sleep therapy data into a manufacturer database (e.g., EncoreAnywhere®, a web-based database provided by Royal Philips Electronics). Here, the consumer has no access to their own data, and full control over the database is vested in the equipment company. The database administrator at the equipment company may not even be a medical professional, but they access the database and may have the ability to grant access to others without the consumer's knowledge or authorization. If the consumer switches to another equipment company the past data typically remains with the previous company, and is lost to any future point-of-care provider. These current practices do not recognize the consumer's rights to protect the privacy/security of their own electronic data, and are not HIPAA HITECH compliant.

There still exists in the art, accordingly, a need for the collection of home sleep therapy data to improve overall scientific knowledge while concurrently acknowledging privacy and security concerns and affording consumers control over their own health data. The need in the art extends to systems and devices that provide for one or more or all of the following features: improved quality and efficiency through the elimination of unnecessary care; reduction of chronic health conditions through disease management; cost control for sleep disorders; information technology with centralized electronic medical records; secure storage of electronic personal health information; coordination of care to provide timely access or availability; and encouragement of consumer-driven healthcare.

SUMMARY OF THE INVENTION

Aspects of the present invention relate to methods and systems for diagnosing and treating sleep disorders including, but not limited to, obstructive sleep apnea.

In accordance with one aspect of the present invention, a method for diagnosing and treating sleep disorders with a sleep therapy auto-titrator for in-home use by the patient comprises collecting, recording, and analyzing sleep data from the patient in real time with the auto-titrator; providing corrective action in real time to the patient to mitigate sleep events based upon the collected sleep data; transmitting, via a global computer information system, the collected sleep data to a remote server for storage; analyzing the stored sleep data with a computer programmed with an algorithm to monitor therapy effectiveness daily and for identifying one or more therapy intervention recommendations; and providing an alert to at least one of the patient or a sleep therapy professional associated with the patient communicating the one or more intervention recommendations.

Another embodiment comprises a system for diagnosing and treating sleep disorders. The system includes a sleep therapy auto-titrator configured for connection to a sleeping patient, for collecting, recording, and analyzing data from the patient in real-time, for providing corrective action in real-time to mitigate sleep events based upon the collected data, and for transmitting the collected data via a global computer information system. The system also includes a remote computer memory connected to the global computer information system for receiving and storing the collected sleep data transmitted by the sleep therapy auto-titrator. Additionally, the system includes a computer processor programmed with an algorithm to monitor therapy effectiveness daily, for analyzing the stored sleep data and for identifying one or more therapy intervention recommendations. Also included is an alert transmitter configured for transmitting an alert to at least one of the patient, or a sleep therapy professional associated with the patient, the alert comprising the one or more intervention recommendations.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The various aspects of the present invention relate generally to novel methods and systems for diagnosing and treating sleep disorders, especially obstructive sleep apnea. Electronic data is collected from home devices and from multiple sources. Computer applications create a real-time personalized dashboard of unique reports and indices in a secure web site. The methods provide care management with unique quality scores and programmed "Therapy Interventions." Home sleep therapy data is populated into personal electronic medical records. The present invention provides a complete sleep disorder management program built around a novel methodology combined with HITECH solutions. The new best practices disclosed herein are designed to change the clinical practice paradigms for sleep disorders.

Input Sources of to the Present Invention

Figure 1:
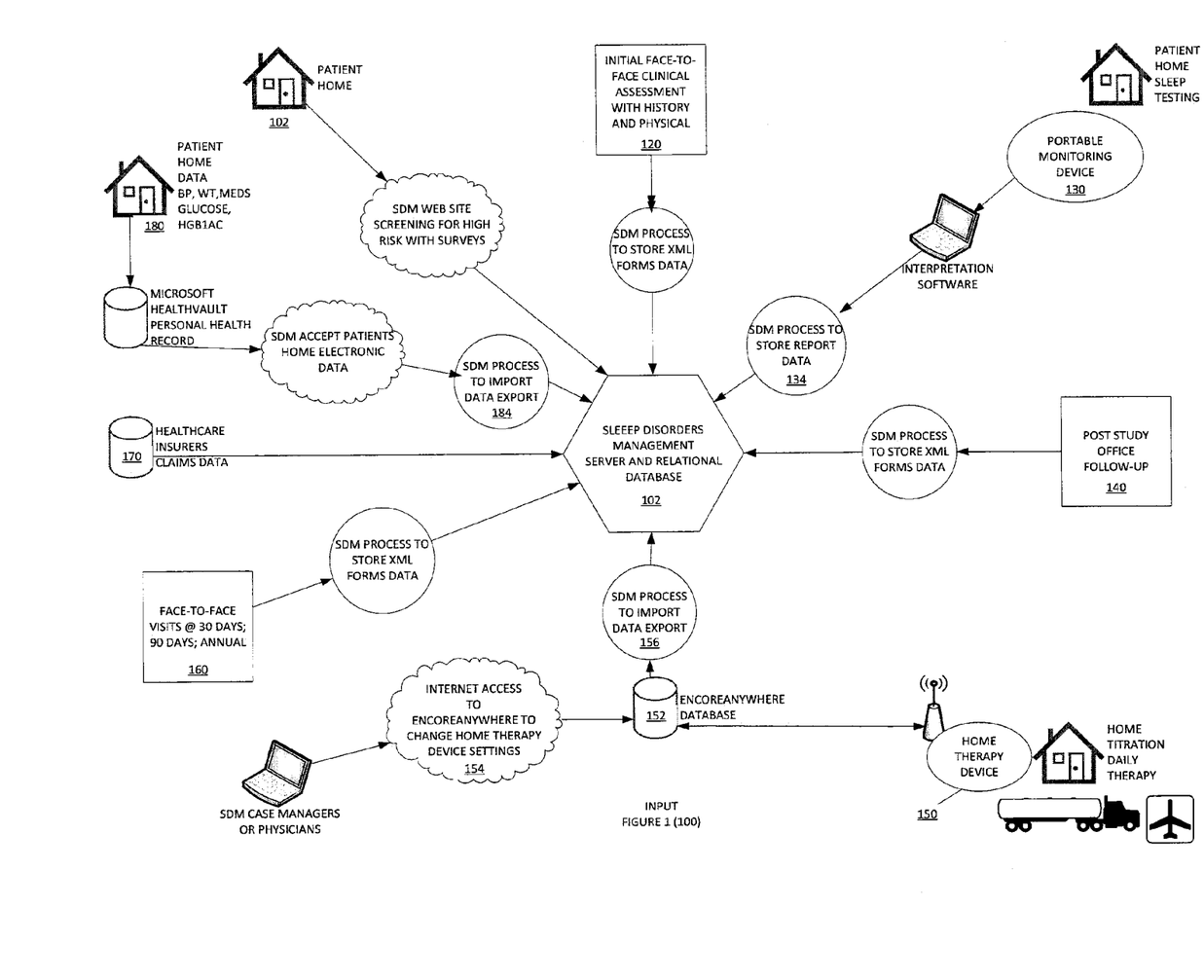
FIG. 1 is an exemplary schematic diagram of various input sources in accordance with aspects of the present invention.

Referring now to the drawings, FIG. 1 illustrates the multiple input sources 100 incorporated by the present invention. Each of the individual sources of data displayed by FIG. 1 is an input which can be received and processed by Server and Relational Database 102, such as provided by Sleep Disorders Management$^{SM}$ (SDM$^{SM}$) of Wilmington, Del. ("SDM Database"). The patient-oriented approach of the instant invention begins with an in-home screening 104 of the patient. In-home screening 104 may be accomplished by surveying through either a self-insured employer wellness program or a chronic disease care management program outsourced by the insurer. The surveying may include a screening conducted during a health fair or by providing a simple online survey distributed as part of the wellness program. In this regard, the present invention markedly improves consumer access by eliminating multiple steps compared to prior art process.

Upon the identification of a potential sleep disorder, the consumer may be given a demonstration (in person or online video) and a home sleep study kit, which initiates the coordination of care. In addition to identifying an undiagnosed sleep disorder consumer by using this type of screening, the primary care physician (PCP) or specialist can also refer a consumer into the care management program. These educational screening opportunities counteract the lack of understanding and awareness, and additionally provide SDM Database 102 with an initial population of data representing signs and symptoms suggesting a risk level for sleep apnea.

An initial face-to-face clinical assessment 120 may also be conducted. In one embodiment according to the present invention, comprehensive sleep history and physical data may be collected in real time during clinical assessment 120 on XML forms, which automatically populate SDM Database 102 using a computer software application, such as software created by Sleep Disorders Management. The saved XML forms may additionally include consumer digital photos and a bar code system that tracks the encounter time spent with the patient.

During an in-home sleep testing step 130 for the diagnosis of sleep apnea, case managers provide testing equipment, and preferably teach the consumer how to properly apply equipment sensors before the consumer sleeps. A high quality portable monitor such as an Alice PDx diagnostic system, from Philips Healthcare of Best, The Netherlands, is a cost-effective and convenient alternative to expensive sleep centers. In-home sleep testing 130 eliminates the initial PSG for a diagnosis used in the conventional process, and establishes the untreated AHI and diagnostic data stored in SDM Database 102. A bar code system tracks the equipment and location real-time to be displayed on a video monitor system along with encounter times.

A processing step 134 is then employed to store the raw signal data on a terminal server for multi-user access. First, the case manager accesses the raw signal data and edits the scoring of respiratory events. A preliminary report is produced using, for example, Alice 5 software. Second, the physician accesses the edited raw signal data for a final interpretation. The final report is created by the physician. This data is stored within the patient folder of data and reports. The data is available for storage in SDM Database 102 along with a comparison of case manager to physician scoring. Time tracking may be established according to the conventional computer system creation time of files.

A post study follow-up step 140 includes interim history and physical data collected real time during the visit on XML forms, which may automatically populate the SDM Database using a computer software application, such as that created by Sleep Disorders Management. A bar code system may track the encounter time spent with the patient.

At the outset of a daily in-home titration 150, the consumer is provided with an auto-titrator, such as for example, a Philips® Respironics System One sleep therapy platform and a cellular modem. A respiratory therapist preferably performs a fit and comfort selection step in order to determine the best interface determined by the consumer. The characteristics monitored and stored by the auto-titrator machines include usage times, therapy flags, and pressure data. The HITECH machine connected to a wireless cellular modem may be configured to transmit data daily into the manufacturer's database.

Figure 7:
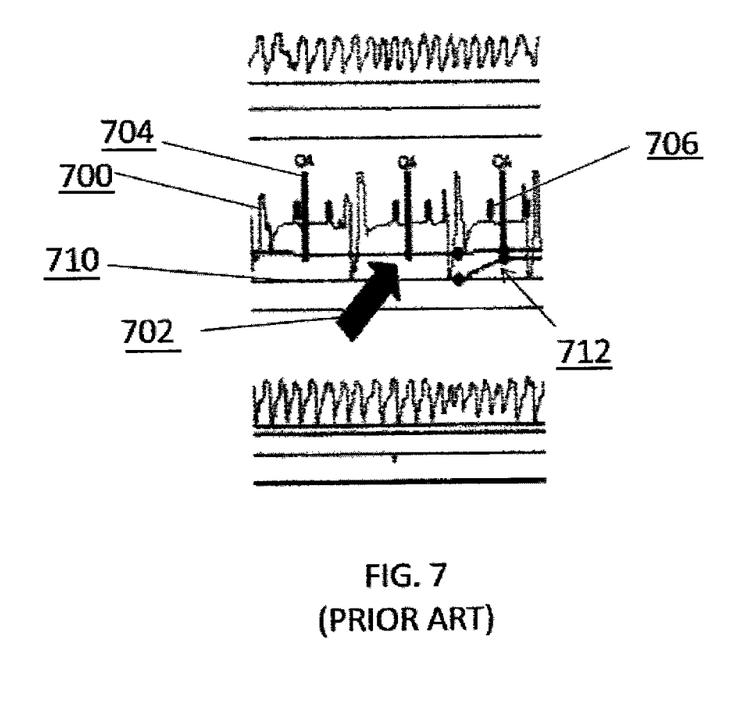
FIG. 7 depicts an exemplary readout of information captured by an auto-titration machine.

The present invention provides a degree of monitoring, analysis, and adjustment superior to a one-time study used to calibrate a fixed pressure machine. Monitoring sleep therapy effectiveness daily from home sleep therapy equipment configured to adjust treatment pressures continuously is more analogous to receiving a sleep lab CPAP titration study daily. For ease of illustration, an exemplary prior art readout from an exemplary machine configured to make such automatic adjustments is shown in FIG. 7. The graph of airway pressure 700 illustrates an obstructed airway (OA) at arrow 702. Periods of apnea are marked with OA Flag 704 when the airflow is reduced by 80% for 10 seconds or there is no airflow for 10 seconds. Vertical marks 706 identify when the sleep therapy machine provides puffs of air into the airway. If the puffs do not lead to a significant flow of air, then the apnea is considered a sign of an obstructed airway and marked "OA." Auto-titration may respond, for example, to two such OAs within three minutes with an increase in pressure. Machine air pressure graph 710 illustrates a 1 cm increase in pressure that is automatically provided over a 15 second interval at inflection 712.

Automated adjustment eliminates the need for a sleep lab CPAP Titration in the conventional process. Relatedly, "Therapy Errors" due to poor quality titrations by an unqualified or under qualified technician are eliminated by the very high inter-scorer reliability of the HITECH machine with a reliable computer algorithm. A bar code system tracks the device times and dates real-time to be displayed on a video monitor system along with the 1st Titration Night Follow-Up.

Figure 5:
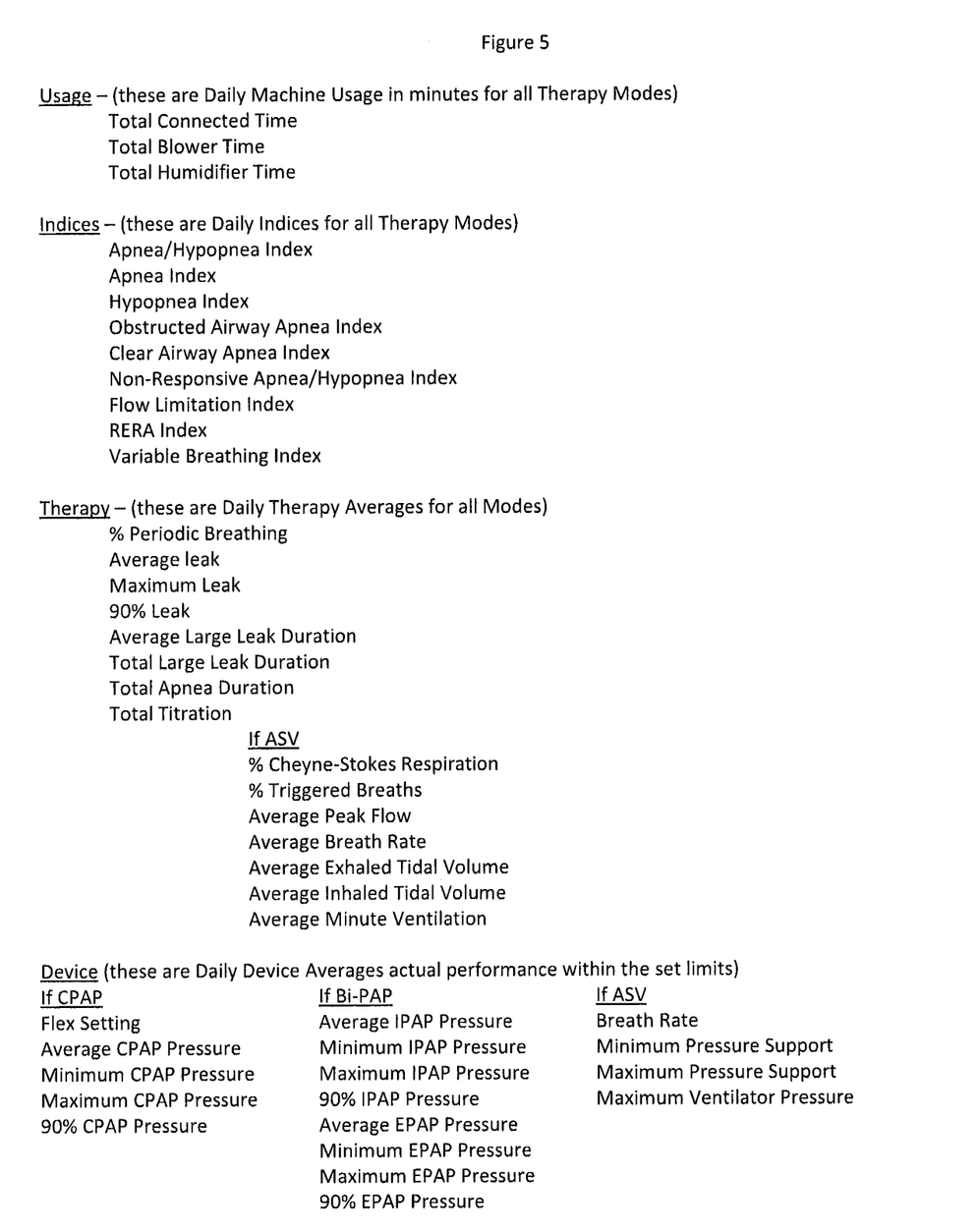
FIG. 5 is a list of exemplary data that may be captured from an in-home auto-titrator.
Figure 6:
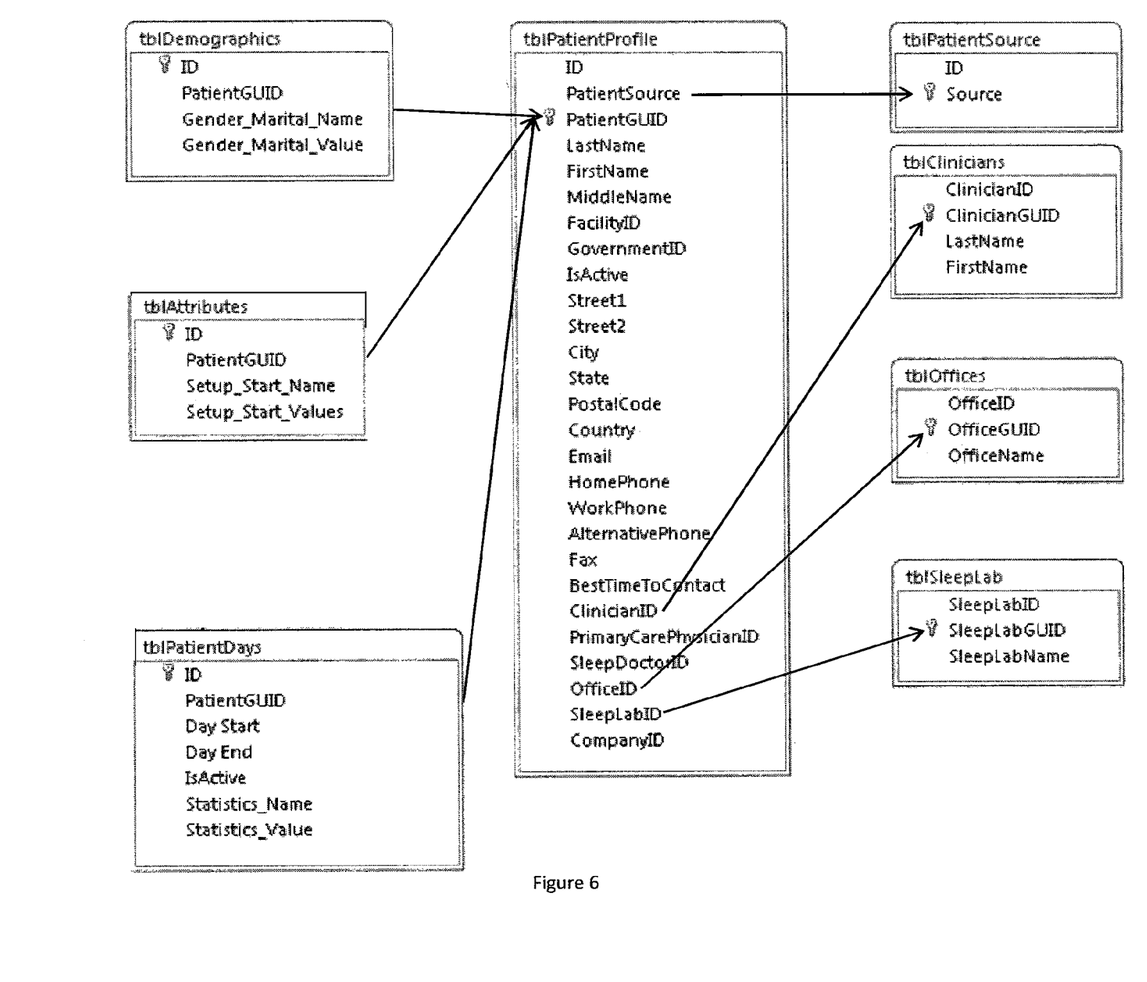
FIG. 6 is an exemplary database schema for the SDM Database discussed herein.

In a preferred embodiment, SDM Database 102 receives a daily data export 152 from the HITECH machine manufacturer's database. Data may include, for example, information relating to the parameters listed in FIG. 5. Prior to importing the data, daily data export 152 is processed to provide compatibility with SDM Database 102 by a software application 156 that captures, stores, and changes the format of the electronic data collected from the consumer's home sleep therapy device. The data is stored in SDM Database 102 and ready for further calculations and analysis. An exemplary partial database schema for SDM database is shown in FIG. 6.

Therapy settings can be adjusted remotely by SDM case managers in an call center 154 accessible by the consumer by activating a request for assistance, similar to services adapted to transmit emergency communications in automobiles, such as the ONSTAR® service. For example, if a patient has Low Hours/Day usage suggesting poor compliance, an alert may flag the SDM case manager to contact the consumer. If the patient complains of side effects like airway drying, then the humidity setting may be adjusted remotely and transmitted by modem to the machine. The remote system may be used to implement remote prescription changes, monitoring of compliance, notify patients of ineffective therapy based on therapy flags or equipment problems, and/or provide monthly therapy summaries.

Figure 2:
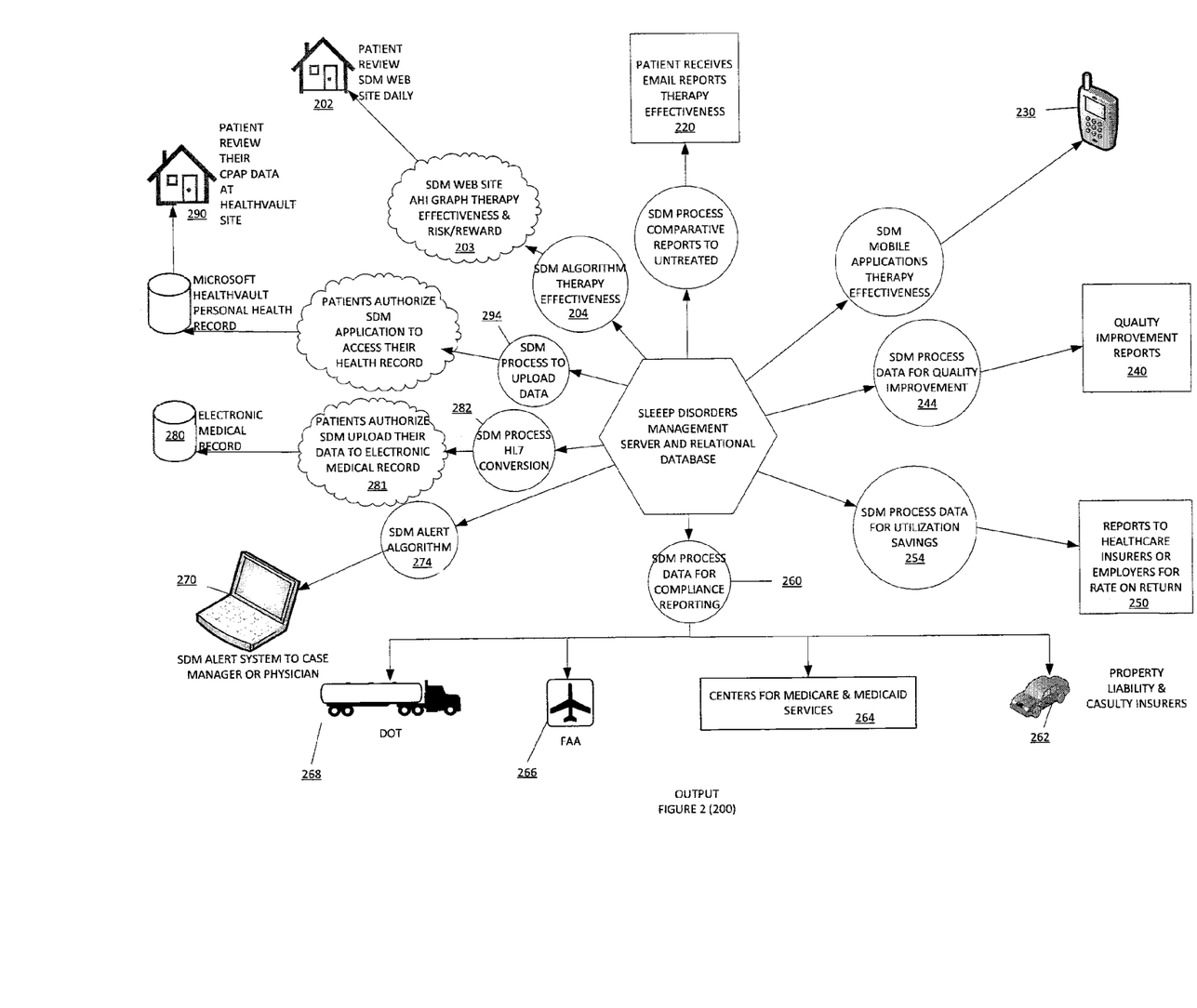
FIG. 2 is an exemplary schematic diagram of the data and reports generated in accordance with aspects of the present invention.

Summaries of progress and compliance may be collected at subsequent visits of 30 days, 90 days, and annually 160 in real time during the visit on XML forms which automatically populate SDM Database 102. A bar code system may track times and dates for follow-up visits. Turning briefly to FIG. 2, summaries of progress and compliance 160 are particularly desirable for compliance reporting analysis 260.

Healthcare insurer claims data 170 is accepted and stored as "de-identified" data (data that has been separated from consumer identification data) in SDM Database 102. The unique codes necessary to cross link the data to the correct consumer are preferably kept secure.

Also preferably imported into SDM Database 102 is Microsoft HealthVault home electronic data 180 from other home electronic devices such as weight scales, glucose meters, Hemoglobin A1c, and blood pressure monitors.

The process 184 to import the MICROSOFT® HEALTH-VAULT® data 180 into SDM Database 102 is, in an exemplary embodiment, a software application created by Sleep Disorders Management called "AHI Sleep Disorders Management." The consumer may then be given the option to approve the capture and use of their data back into the SDM SharePoint web site for their personalized reports. When authorized, the "AHI Sleep Disorders Management" computer application exports data out of the member's personal record back to SDM Database 102 for additional analysis and processing.

Outputs of the Present Invention

Figure 8:
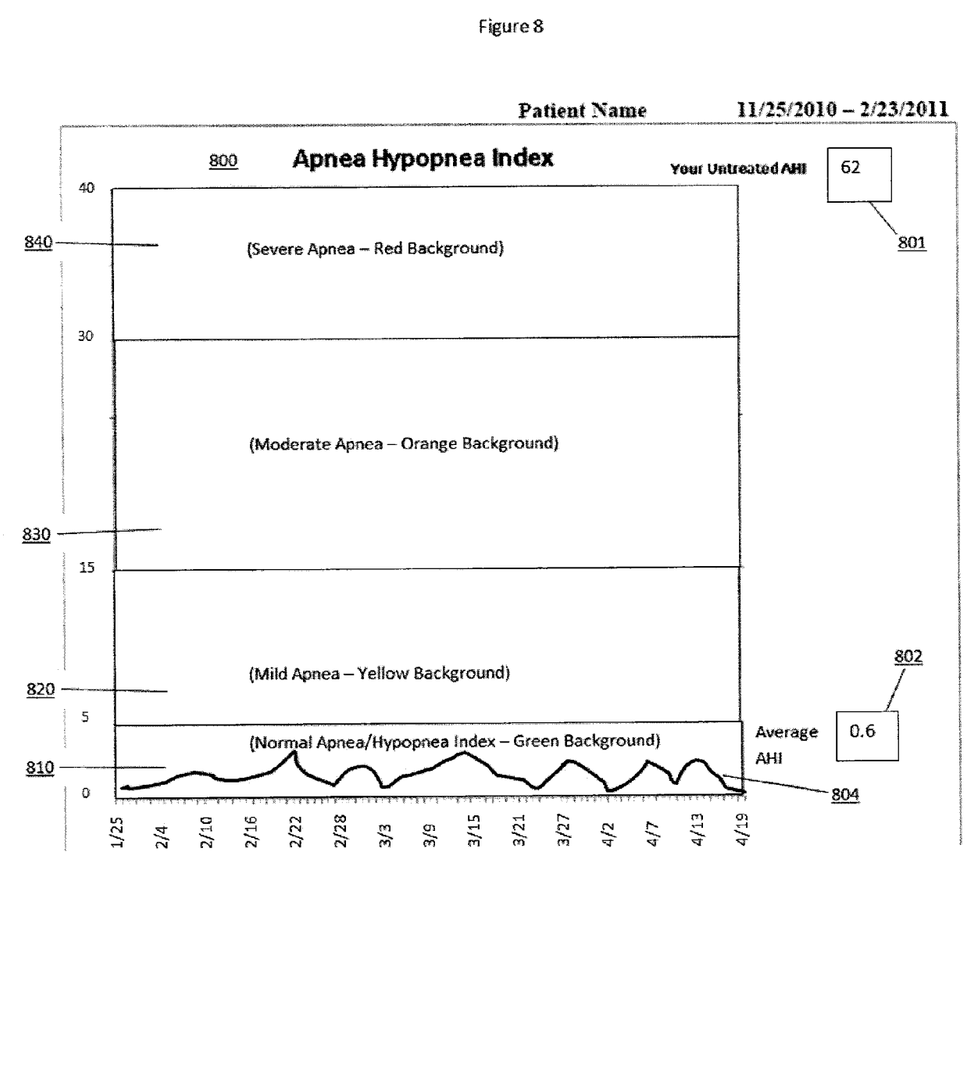
FIG. 8 depicts an exemplary AHI chart.

SDM Database 102 provides consumer education 202 in a secure web site. Consumer education 202 may be oriented to empower the consumer and encourage active participation in disease care management. Additionally, it may present a summary of the literature for the consumer and physicians to easily review. For these purposes, the invention provides the consumer with access to their home sleep information through reports located at a HIPAA HITECH compliant password protected SharePoint web site that is private and secured with secure sockets layer (SLL) encryption. The reports may be programmed to automatically populate with the consumer's personal data from the relational database after computer application analysis. An application 203 displays results from personal sleep therapy data in a "Dashboard" visual. The Dashboard preferably displays sleep therapy data as user-friendly charts and tabular format for the consumer. A chart, such as for example chart 800 shown in FIG. 8, provided in the Dashboard preferably compares a high untreated AHI 801 to a range of daily AHI obtained during therapy in a linear graph 804. The average AHI 802 for the selected period may also be displayed. The chart represents, for example, regions of normal 810, mild apnea 820, moderate apnea 830, and severe apnea 840 ranges with background colors of, i.e., green, yellow, orange, and red respectively. The chart combines past untreated AHI to the present real-time data to measure therapy effectiveness. The untreated AHI is displayed to remind the consumer where they started.

Sleep therapy data may be combined with information from other home digital devices (glucose, Hemoglobin A1c, blood pressure, and weight) collected at home or at the facilities of third party providers (such as, for example, blood pressure captured and transmitted from a machine at a local retail store convenient to the patient) and downloaded into SDM Database 102. An informational display application 204, such as an application including the display depicted in FIG. 8, then provides an indication of therapy effectiveness. The information display application may provide a a multi-factorial analysis of sleep therapy data indices (OA, CA, PB, AHI, RDI), glucose, Hemoglobin A1c, blood pressure, and weight and provide a "AHI Health Risk—Reward" number, for which an exemplary embodiment is described herein below. This analysis may include a matrix of consumer age, disease, and multiple diseases matched to odds extracted from scientific literature to calculate the consumer's personal odds to develop, among other conditions, Sudden Death, Stroke, Auto Accident, Work Place Accident, Heart Attack, and Complication of Diabetes (cataracts, renal failure). AHI level untreated will be used for an initial "AHI Health Risk—Reward" number and it will be compared to a real-time "AHI Health Risk—Reward" number automatically calculated daily during treatment. Ideally, the ratio of (health risk during treatment/health risk before treatment) is less than one.

An exemplary AHI Health Risk-Reward number Risk Reward Ratio may be calculated starting with an untreated risk rate for sudden death, stroke, auto accident, and work place accident from published sources. For example, the numbers in Table 1, below, were extracted from a review of 260 peer-based scientific articles

TABLE 1

|  | Untreated Risk Rate | Green Arrow AHI Range | Red Arrow AHI Range | Treated Risk Rate |
|---|---|---|---|---|
| Sudden Death | 257% | 0-14.9 | 15-200 | 21% |
| Stroke | 333% | 0-19.9 | 20-200 | 1% |
| Auto Accident | 433% | 0-14.9 | 15-200 | 1% |
| Work Place Accident | 250% | 0-14.9 | 15-200 | 1% |

Figure 9A:
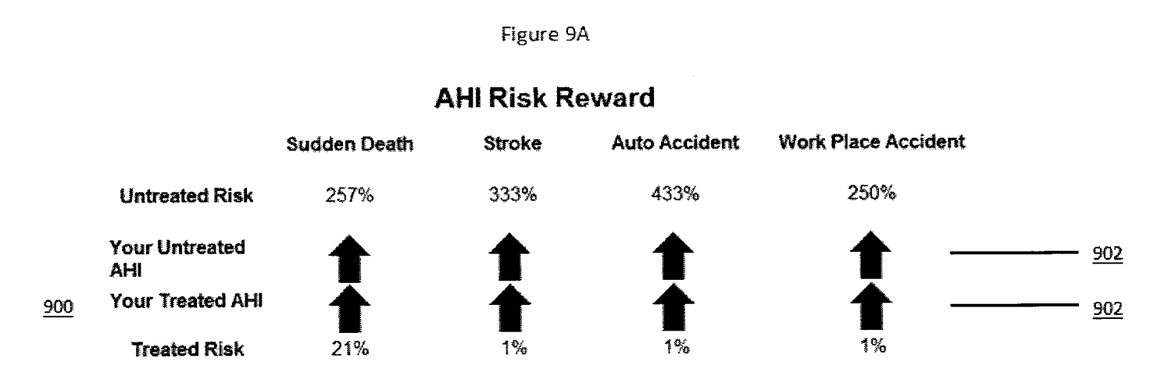
FIGS. 9A and 9B depict exemplary visual presentations for AHI Risk-Reward Ratios.
Figure 9B:
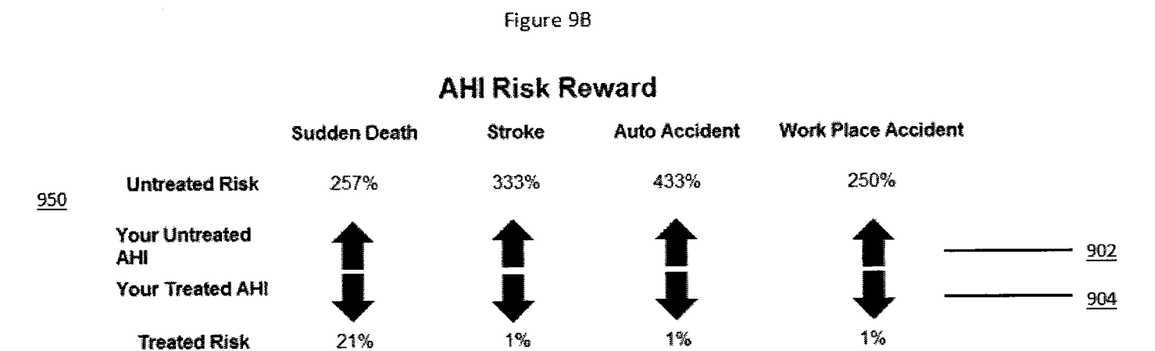

The patient's untreated AHI may be averaged, for example, over a default period of the last 30 days or any range of starting and ending dates. The user is given a comparison of their untreated AHI to the AHI that produces the increased risk, such as the exemplary visual presentation 900 and 950 shown in FIGS. 9A and 9B, respectively. If the patient's AHI is greater than the risk point, a red risk arrow 902 is displayed pointing upward to the higher number. If the patient's AHI is lower than the risk point, a green risk arrow 904 is displayed and points downward to the lower number. The Rates and ranges are programmable and can be changed as the field of information changes. For example, if an untreated AHI was 62, then all four Red risk arrows point up to the high Untreated Risk Rates, as shown in chart 900 in FIG. 9A. Similarly, for example, at the beginning of treatment, if the Treated AHI average is still above 20 in all categories, the red upward arrows 902 will also be displayed in the Treated Risk Rate row, as shown in FIG. 9A. But, for example, as shown in FIG. 9B, where the patient's last 30 days of sleep therapy treatment results in a Treated AHI average of 0.5, all four green risk arrows 904 point down to the low Treated Risk Rates. The Treated Risk Rate/Untreated Risk Rate is less than one to demonstrate the reward of effective therapy. These arrows may be provided in real time in the dashboard accessible by the patient and may change day to day based upon the average Treated AHI.

Daily programmed Therapy Interventions 220 are sent to the consumer (and others authorized by the consumer) to provide relevant alerts and general information regarding the effectiveness of the therapy. Exemplary Therapy Interventions are further discussed below. Therapy Interventions 220 are provided by emails, text, short message services, as well as by phone and tablet applications 230 regarding therapy issues.

Key performance indicators 240 for quality improvement are generated from the stored data in the relational database and displayed on video monitors in the office for live real-time tracking of, for example but not limited to, Service Time Intervals, Inventory Tracking, Interscorer Quality Monitoring, Patient Compliance, and Study Quality. Service Time Intervals may include established time periods for an initial clinical assessment, a physician interpretation, a post study follow-up visit, and therapy. Inventory Tracking notifies office personnel when a device has been checked in, cleaned, and (if applicable) subjected to repairs and/or annual maintenance. The Interscorer Quality Monitoring compares the AHI determined by a technologist to the AHI determined by the physician. Acceptable ranges for score variance will vary by range of AHI, so for example, acceptable quality for AHI of: 0-5=+1; 6-15=+2; 16-30=±5; and >30=±6. The Patient Compliance indicator provides trending usage data (e.g., notification of usage approaching or greater than 70% of the prescribed nights for at least 4 hours/night). Study Quality provides indications of: 1) study failures, e.g., where recorded times are less than 2 hours, malfunction of any associated equipment (effort belts, $SpO_2$ sensor, airflow sensor), or where no heart rate is recorded; 2) numbers and rates of retests (and, relatedly, whether the retests are due to patient or equipment issues); and 3) patient complaint tracking (by number and rate).

In a preferred embodiment, the SDM Database calculates a real-time "Executive Dashboard" 244 which tracks corporate key performance indicators and outcome measures. For example, the "Executive Dashboard" may display the % of the care management population with "AHI Health Risk—Reward", "AHI Utilization—Benefit", and "AHI Cost—Savings" values less than one. The results can also be filtered by payers or customers.

In another preferred embodiment, best practices are employed to control costs. Key Performance Indicators 250 for Utilization Management are generated from a meta-analysis of the stored relational database comparing AHI levels before treatment to AHI levels during therapy against any parameter collected in the relational database including screening risks, symptoms, medical history, associated diseases, physical exam findings, therapy indices, and others.

A meta-analysis of utilization data 254 from the healthcare insurers and the stored relational database may be performed and categorized by: Inpatient; Outpatient; and Emergency Department utilization. Analysis 254 may stratify the utilization by therapy indices (OA, CA, PB, AHI, RDI). An exemplary Inpatient calculation includes sorting by diagnosis codes, lengths of stay, and number of admissions. Analysis 254 may also include a comparison of costs 2 years before treatment vs. costs during therapy. Analysis 254 produces an "AHI Utilization—Benefit" number so the cost of diagnosis and treatment can be compared to the utilization reduction Benefit. The ratio of (current utilization/past utilization) should be less than one.

Analysis 254 may also include tracking the current costs for diagnosis and treatment compared to the then-current usual and customary costs which, for example, at the time of filing the present application are between $6,000 to $8,000. An "AHI Cost-Savings" number may be calculated for each individual. For example, the (current costs/$8,000) should preferably be less than one.

Preferably, a compliance algorithm 260 analyzes the SDM relational database for compliance reporting to multiple third parties such as, for example, Department of Transportation (DOT), Federal Aviation Administration (FAA), Centers for Medicare & Medicaid (CMS), and property liability & casualty insurers. Compliance algorithm 260 may automatically calculate the compliance rates and monitoring dates to report compliance with specific guidelines which affect certification and reimbursement.

In yet another preferred embodiment, compliance data is automatically transferred by a property & liability insurer compliance reporting algorithm 262 to property liability & casualty insurers requirements for drivers who have past auto accidents and suspected sleep apnea. Compliance could result in lower premium adjustments and continued insurance coverage. Non-compliance could result in higher premium adjustments or discontinued insurance coverage. Compliance data may similarly be transferred by: 1) Medicare/Medicaid reporting algorithm 264 to the Centers for Medicare & Medicaid; 2) FAA reporting algorithm 266 to the FAA regarding guidelines which may affect the certification of a commercial pilot; and 3) DOT reporting algorithm 268 regarding guidelines which may affect the certification of a commercial driver. The requisite algorithm, may for example, comprise a code inserted in the Database 102 indicating that Medicare/Medicaid, FAA, and/or DOT reporting is required, and programmed instructions to transmit any reported data in such flagged files periodically or whenever new data is entered.

Interpretation algorithm 270 automates the interpretation of daily data from the SDM relational database and the rules engine automatically creates "Therapy Interventions and Alerts" for case managers and physicians, such as but not limited to those discussed below.

Figure 3:
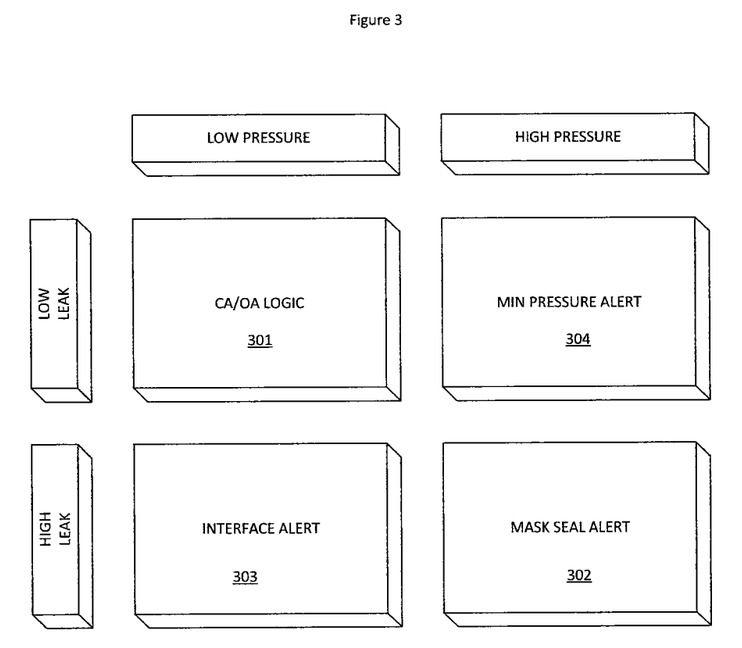
FIG. 3 illustrates an exemplary decision matrix of leak rates versus average machine pressures delivered during therapy which provides four matrix pathways in accordance with aspects of the present invention.

"Therapy Interventions and Alerts" may be generated by alerting algorithm 274, which employs a rules-based analysis of the data in SDM database 102. The matrix employed in the rules-based analysis conducted by alerting algorithm 274 is illustrated in FIG. 3. For example:

High Leak/High Pressure Index 302 suggests a mask issue or mouth breathing with a nasal mask. An intervention response 404 (shown in FIG. 4) may include a mask check by the DME provider and possible chin strap.

High Pressure/Low Leak Index 304 would signal a Minimum Pressure alert 405.

Low Pressure/High Leak Index 303 would signal an Interface Alert 407.

Low Pressure/Low Leak would start the CA/OA Logic 301.

Figure 4:
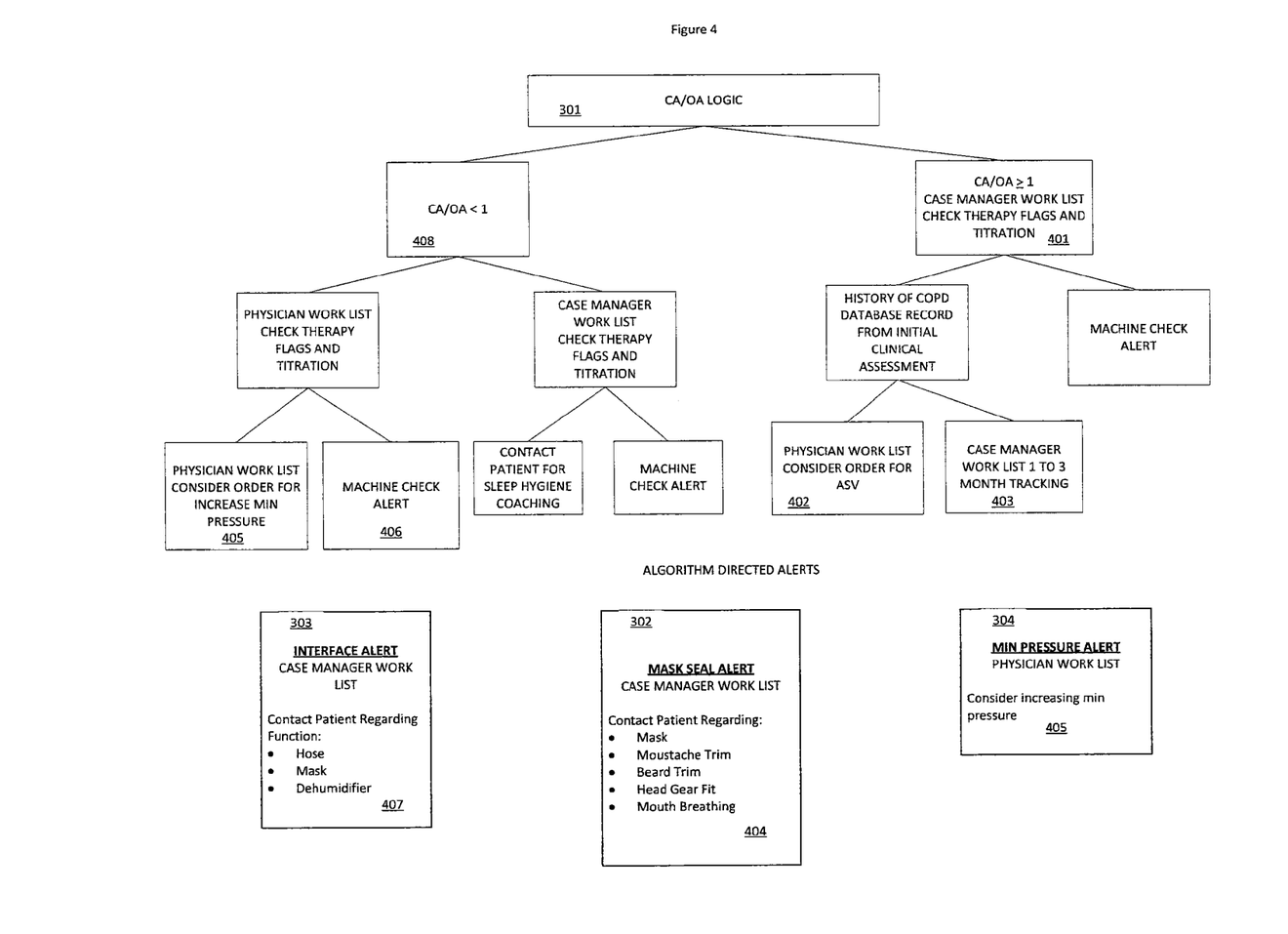
FIG. 4 is an exemplary logic diagram relating to each of the four matrix pathways illustrated in FIG. 3.

FIG. 4 depicts the CA/OA (clear airway/obstructed airway) algorithm components (one of the four possible pathways of the matrix illustrated in FIG. 3) with intervention outcomes. FIG. 5 identifies the Clear Airway Apnea Index (CA) and Obstructed Airway Apnea Index (OA) as data points collected into the relational database daily. Any date range of numbers (few days, week, month, several month, to years) can be averaged and then divided to calculate the CA/OA Index for trending.

A CA/OA Index (401)>1 with increasing Periodic Breathing suggests more central apnea issues. One possible intervention response 402 may be to consider an Automatic Servo Ventilation (ASV) unit to provide the patient a minimum number of breaths. Another intervention 403 could include monitoring for 1 to 3 months if the patient had a history of Chronic Obstructive Lung Disease (COPD).

A CA/OA Index (408)<1 can be seen when the OA is increasing. An AHI Distribution Index higher during the first half of sleep vs. the last half of sleep time suggests that the baseline auto-titrator pressure is starting too low. An alert 405 signals the physician to check the trend and consider an intervention response to remotely change the minimum pressure setting which will transmit by modem to the machine automatically. If no titration is seen for marked OA events, then another intervention 406 may be to issue a machine alert for the DME provider to check the function of the auto-titrator.

A Zero CA/OA Index may suggest that the treatment pressure is very low or the home study provided a false positive, so the intervention response may include a manual review for OA Flags. The presence of OA Flags would suggest a low treatment pressure, and no OA Flags would suggest a false positive study.

Turning back to FIG. 2, in a preferred embodiment, "AHI Sleep Disorders Management" solution automatically uploads sleep therapy data (such as, in HL7 format) from SDM database 102 to a universal electronic medical record 280 using a conversion application 282 (for example, using a custom application created by Sleep Disorders Management, but the conversion application may be any set of computer instructions for converting data in one output format to a format required by the universal electronic medical record). The term "universal electronic medical record" refers to any electronic medical record accessible to or used by multiple medical services providers, including records compliant with any standards that are now or may later be published for qualifying such records.

Home sleep therapy data is collected and uploaded into a universal electronic medical record 290. This returns the control of home therapy data back to the consumer in a HIPAA HITECH Act complaint manner. The gathering of data from diverse systems also gives the point of care provider a continuum of healthcare data and information. This data also gives researchers the ability to study therapy effectiveness rather than simply consumer compliance (which was all that was available during past studies). In this regard, it will also improve scientific knowledge.

It should be understood that any of the method steps and calculations described herein may be performed on a special purpose computer, such as a general purpose computer programmed with software and/or hardware, having embedded therein instructions for the computer to perform the specified steps. Furthermore, any displays depicted herein may be generated by a computer connected to and accessible via a computer network, such as but not limited to the Internet or World Wide Web, and may be generated in response to a patient or healthcare provider accessing the computer through the computer network and providing identification, such as a secure username and password, that permits access to the information. The invention is not limited to the use of any particular display format, computer language, or type of network, and those of skill in the art of computer design and programming will find sufficient information disclosed herein, and in the provisional application incorporated herein by reference, to facilitate the disclosed functionalities.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for diagnosing and treating sleep disorders with a sleep therapy auto-titrator provided for in-home use and adapted to be connected to the patient during sleep, the method comprising:
   (a) collecting, recording, and analyzing sleep data from the patient in real time with the auto-titrator;
   (b) providing corrective action in real time to the patient to mitigate sleep events based upon the collected sleep data;
   (c) transmitting, via a global computer information system, the collected sleep data to a remote server for storage;
   (d) analyzing the stored sleep data with a computer programmed with an algorithm to monitor therapy effectiveness daily and for identifying one or more therapy intervention recommendations;
   (e) providing an alert to at least one of the patient or a sleep therapy professional associated with the patient and communicating the one or more therapy intervention recommendations;
   (f) compiling stored sleep data for a plurality of sleep periods for the patient;
   (g) compiling at least a linear timeline graph comparing stored sleep data for a first sleep period to sleep data associated with a one or more later sleep periods, wherein the linear timeline graph visually indicates periods of normal sleep, mild apnea, moderate apnea, and severe apnea using color coding; and
   (h) providing access to at least one of the patient or the sleep therapy professional to at least the linear timeline graph.

2. The method of claim 1, further comprising:
   (i) collecting home electronic health data metrics from a patient selected from the group consisting of: glucose, hemoglobin A1c, blood pressure, weight, and a combination of one or more thereof;
   (j) analyzing the home electronic health data metrics together with the stored sleep data for the plurality of sleep periods with a computer programmed to determine a health risk-reward number for each sleep period;
   (k) providing a ratio of a health risk-reward number for a particular sleep period or average of multiple sleep periods during which the patient is undergoing sleep therapy treatment, divided by a health risk-reward number for a sleep period prior to the patient undergoing treatment.

3. The method of claim 2, further comprising:
   (l) compiling historic healthcare service utilization cost data associated with the patient for a time period prior to undergoing sleep therapy;
   (m) collecting healthcare service utilization cost data associated with the patient for a time period during which the patient is undergoing sleep therapy;
   (n) providing a ratio of current healthcare service utilization cost/past healthcare service utilization cost.

4. A system for diagnosing and treating sleep disorders, the system comprising:
   a sleep therapy auto-titrator adapted for connection to a sleeping patient, for collecting, recording, and analyzing data from the patient in real-time, for providing corrective action in real-time to mitigate sleep events based upon the collected data, and for transmitting the collected data via a global computer information system;
   a remote computer memory connected to the global computer information system for receiving and storing the collected sleep data transmitted by the sleep therapy auto-titrator, the computer memory comprising stored sleep data for a plurality of sleep periods for the patient;
   a computer processor programmed with an algorithm to monitor therapy effectiveness daily, for analyzing the stored sleep data and for identifying one or more therapy intervention recommendations, the computer processor programmed to compile and store a linear timeline graph depicting stored sleep data for a first sleep period and sleep data associated with a prior sleep period, the linear timeline graph comprising a visual indication of periods of normal sleep, mild apnea, moderate apnea, and severe apnea, wherein at least one of the patient or the sleep therapy professional has access to the one or more graphs or tables; and
   an alert transmitter configured for transmitting an alert to at least one of the patient, or a sleep therapy professional associated with the patient, the alert comprising the one or more intervention recommendations.

5. The system of claim 4, wherein the computer memory further comprises stored home electronic health data metrics from a patient, the home electronic health data metrics selected from the group consisting of: glucose, hemoglobin A1c, blood pressure, weight, and a combination of one or more thereof, and the processor is further programmed to analyze the home electronic health data metrics together with the stored sleep data for the plurality of sleep periods, to assign a health risk-reward number to the patient for each sleep period, and to provide a ratio of the health risk-reward number or an average of multiple health risk-reward numbers for a period or periods during which the patient was undergoing sleep therapy, and the health risk-reward number for a period prior to the patient undergoing sleep therapy.

6. The system of claim 5, wherein the computer memory further comprises stored historic healthcare service utilization cost data associated with the patient for a period prior to undergoing sleep therapy and healthcare service utilization cost data associated with the patient during a period in which the patient in undergoing sleep therapy, and the processor is further configured to determine a ratio of current healthcare service utilization/past current healthcare service utilization.

7. The system of claim 6, further comprising a computer programmed to upload the patient sleep data to a universal electronic medical record.

8. The method of claim 1, further comprising a patient screening step comprising collecting and storing comprehensive sleep history information and clinical exam data for the patient, and a diagnosis step, comprising providing the patient with a portable sleep monitor and conducting an unattended home sleep study of the patient, wherein the analyzing the stored sleep data further comprises analyzing the sleep history information and clinical exam data against results from the unattended home sleep study and data indicative of therapy effectiveness from the auto-titrator.

9. A system for diagnosing and treating sleep disorders, the system comprising:
  a sleep therapy auto-titrator adapted for connection to a sleeping patient, for collecting, recording, and analyzing data from the patient in real-time, for providing corrective action in real-time to mitigate sleep events based upon the collected data, and for transmitting the collected data via a global computer information system;
  a remote computer memory connected to the global computer information system for receiving and storing the collected sleep data transmitted by the sleep therapy auto-titrator, the computer memory comprising stored comprehensive sleep history information and clinical exam data for the patient, wherein the computer memory comprises stored sleep data for a plurality of sleep periods for the patient;
  a portable sleep monitor adapted for connection to a sleeping patient for conducting an unattended home sleep study and configured to transmit the data from the home sleep study via a global computer information system to the computer memory
    a computer processor programmed with an algorithm to monitor therapy effectiveness daily, for analyzing the stored sleep data and for identifying one or more therapy intervention recommendations, the computer process configured to analyze the stored sleep history information and clinical exam data against results from the unattended home sleep study and data indicative of therapy effectiveness from the auto-titrator and to compile and store a linear timeline graph depicting stored sleep data for a first sleep period and sleep data associated with a prior sleep period, the linear timeline graph comprising a visual indication of periods of normal sleep, mild apnea, moderate apnea, and severe apnea; wherein at least one of the patient or the sleep therapy professional has access to the one or more graphs or tables; and
  an alert transmitter configured for transmitting an alert to at least one of the patient, or a sleep therapy professional associated with the patient, the alert comprising the one or more intervention recommendations.

10. The system of claim 9, wherein the computer memory further comprises stored home electronic health data metrics from a patient, the home electronic health data metrics selected from the group consisting of: glucose, hemoglobin A1c, blood pressure, weight, and a combination of one or more thereof, and the processor is further programmed to analyze the home electronic health data metrics together with the stored sleep data for the plurality of sleep periods, to assign a health risk-reward number to the patient for each sleep period, and to provide a ratio of the health risk-reward number or an average of multiple health risk-reward numbers for a period or periods during which the patient was undergoing sleep therapy, and the health risk-reward number for a period prior to the patient undergoing sleep therapy.

11. The system of claim 10, wherein the computer memory further comprises stored historic healthcare service utilization cost data associated with the patient for a period prior to undergoing sleep therapy and healthcare service utilization cost data associated with the patient during a period in which the patient in undergoing sleep therapy, and the processor is further configured to determine a ratio of current healthcare service utilization/past current healthcare service utilization.

12. The system of claim 11, further comprising a computer programmed to upload the patient sleep data to a universal electronic medical record.

13. The system of claim 4, further comprising a computer programmed to upload the patient sleep data to a universal electronic medical record.

14. The system of claim 9, further comprising a computer programmed to upload the patient sleep data to a universal electronic medical record.

15. The method of claim 1, further comprising uploading the patient's stored sleep data to a universal electronic medical record for the patient.

16. The method of claim 8, further comprising uploading the patient's stored sleep data to a universal electronic medical record for the patient.

17. The method of claim 2, further comprising uploading the patient's stored sleep data to a universal electronic medical record for the patient.

18. The method of claim 3, further comprising uploading the patient's stored sleep data to a universal electronic medical record for the patient.

19. The method of claim 5, further comprising uploading the patient's stored sleep data to a universal electronic medical record for the patient.

20. The system of claim 10, further comprising a computer programmed to upload the patient sleep data to a universal electronic medical record.

* * * * *